(12) United States Patent
Kasahara (10) Patent No.: US 8,437,527 B2
(45) Date of Patent: May 7, 2013

(54) ULTRASOUND DIAGNOSTIC APPARATUS

(75) Inventor: Eiji Kasahara, Mitaka (JP)

(73) Assignee: Hitachi Aloka Medical, Ltd., Mitaka-shi, Tokyo (JP)

( * ) Notice: Subject to any disclaimer, the term of this patent is extended or adjusted under 35 U.S.C. 154(b) by 142 days.

(21) Appl. No.: 13/159,933

(22) Filed: Jun. 14, 2011

(65) Prior Publication Data

US 2011/0311114 A1 Dec. 22, 2011

(30) Foreign Application Priority Data

Jun. 16, 2010 (JP) ................................. 2010-137183

(51) Int. Cl.
*G06K 9/00* (2006.01)
*A61B 8/00* (2006.01)

(52) U.S. Cl.
USPC .......................................... 382/133; 600/443

(58) Field of Classification Search .................. 382/128, 382/129, 130, 131, 132, 133; 600/407, 410, 600/411, 425, 427, 443, 437, 447; 128/915, 128/916, 920, 922; 378/4, 8, 21–27
See application file for complete search history.

(56) References Cited

U.S. PATENT DOCUMENTS

| | | | | |
|---|---|---|---|---|
| 5,766,129 | A * | 6/1998 | Mochizuki ..................... | 600/443 |
| 6,966,878 | B2 * | 11/2005 | Schoisswohl et al. ........ | 600/443 |
| 2005/0049502 | A1 | 3/2005 | Schoisswohl | |
| 2005/0049503 | A1 | 3/2005 | Schoisswohl et al. | |

FOREIGN PATENT DOCUMENTS

| | | |
|---|---|---|
| EP | 1 825 813 A1 | 8/2007 |
| JP | 3537594 B2 | 6/2004 |
| JP | 2005-74225 A | 3/2005 |
| WO | 2006/136988 A2 | 12/2006 |
| WO | 2008/071454 A2 | 6/2008 |

OTHER PUBLICATIONS

Berg, Sevald et al.; "Dynamic Three-Dimensional Freehand Echocardiography Using Raw Digital Ultrasound Data"; Ultrasound in Med. and Biol, 1999, pp. 745-753, vol. 25, No. 5(cited in European Search Report dated Oct. 19, 2011).
European Search Report dated Oct. 19, 2011, issued in corresponding European Patent Application No. 11004601.8.
Chinese Office Action dated Jan. 4, 2013, issued in corresponding Chinese Patent Application No. 201110166353.5, with English translation (19 pages).

* cited by examiner

*Primary Examiner* — Abolfazl Tabatabai
(74) *Attorney, Agent, or Firm* — Westerman, Hattori, Daniels & Adrian, LLP (57) ABSTRACT

A position information attaching unit (13) attaches, to each set of tomographic image data acquired from each scanning plane, position data for identifying a position of the tomographic image data within a three-dimensional region. A pre-memory (14) stores a plurality of sets of tomographic image data in a time-series order. A reconfiguration processing unit (20) uses the respective base images as division units to divide the plurality of sets of tomographic image data stored in the pre-memory (14) into a plurality of image groups. Then, data of a plurality of tomographic images which correspond to one another on a periodic basis are sequentially extracted from the respective image groups, and are stored in a post-memory (26) as one data block. A three-dimensional image-forming unit (28) forms a display image based on the plurality of sets of tomographic image data after reconfiguration stored in the post-memory (26) and while correlating each set of tomographic image data to a position within a display region identified by respective position data.

15 Claims, 8 Drawing Sheets

ULTRASOUND DIAGNOSTIC APPARATUS

BACKGROUND

1. Technical Field

The present invention relates to an ultrasound diagnostic apparatus for forming display images of an object in periodic motion.

2. Related Art

Ultrasound diagnostic apparatuses for forming three-dimensional ultrasound images of tissue in motion, such as a heart, have been known. For example, in a known technique, ultrasonic beams are scanned in a three-dimensional region to acquire echo data from the three-dimensional region, and, based on the acquired echo data, a three-dimensional ultrasound image is formed, to be displayed in real time. However, real-time display has a fundamental constraint in that a tradeoff relationship exists among scan rate, beam density, and beam range.

A technique for preventing the fundamental constraint in real-time display of three-dimensional ultrasound images has also been proposed. For example, JP 3537594B (Patent Document 1) discloses a technique in which a scanning plane is gradually displaced within the three-dimensional region in synchronization with electrocardiographic signals or the like; a plurality of sets of tomographic image data are acquired over a plurality of time phases at respective positions of the scanning planes; and the plurality of sets of acquired tomographic image data are rearranged and reconstructed to form three-dimensional image data (a reconfiguration process or reconstruction process). However, difficulty is encountered in applying this technique to, for example, a fetus, from which electrocardiographic signals may not be obtained directly.

JP 2005-74225 A (Patent Document 2) discloses a technique for reconstruction by performing scanning at certain time intervals, rather than using electrocardiographic signals. However, in this technique, the motion period of an object such as a heart during data acquisition is assumed to be constant. If the motion period of a heart is not constant, the form of the heart in the reconstructed image may be distorted from the actual form of the heart, thereby lowering reliability.

In view of the above-described related art, the inventor of the present invention has performed research and development for a technique of forming ultrasound images by means of a reconfiguration process. In particular, the inventor has performed research and development on a reconfiguration process preferable for an object in a motion having an unstable period.

SUMMARY

The present invention has been conceived through the above-described research and development, and an advantage of the present invention lies in improved reliability of a display image obtained as a result of the reconfiguration process.

According to one aspect of the present invention, there is provided an ultrasound diagnostic apparatus comprising: a probe that emits and receives ultrasonic waves to and from a three-dimensional region including an object in periodic motion; an emission and reception controlling unit that controls the probe such that a scanning plane is displaced over a plurality of periods of the motion so as to form a plurality of scanning planes within the three-dimensional region; a base image searching unit that searches for a plurality of base images from an image string constituted of a plurality of images corresponding to the plurality of scanning planes based on a feature amount relating to the periodicity of the motion; an image reconfiguration unit that divides the image string into a plurality of image groups using the respective base images as dividing units, and extracts from the respective image groups a plurality of images which correspond to one another on a periodic basis; and a display-image-forming unit that forms a display image of the object based on the plurality of images which correspond to one another on a periodic basis, wherein position information for identifying a position of an image in the three-dimensional region is attached to each image obtained from each of the scanning planes, and the display image is formed while each of the plurality of images which correspond to one another on a periodic basis is correlated to a position within a display region identified by respective position information.

According to this aspect of the present invention, it is possible to improve reliability of a display image obtained as a result of the reconfiguration process. For example, it is possible to reduce or eliminate spatial distortion while reducing or eliminating temporal disturbances, and to obtain a display image of very high reliability.

DETAILED DESCRIPTION

Hereinafter, a preferred embodiment of the present invention will be described.

Figure 1:
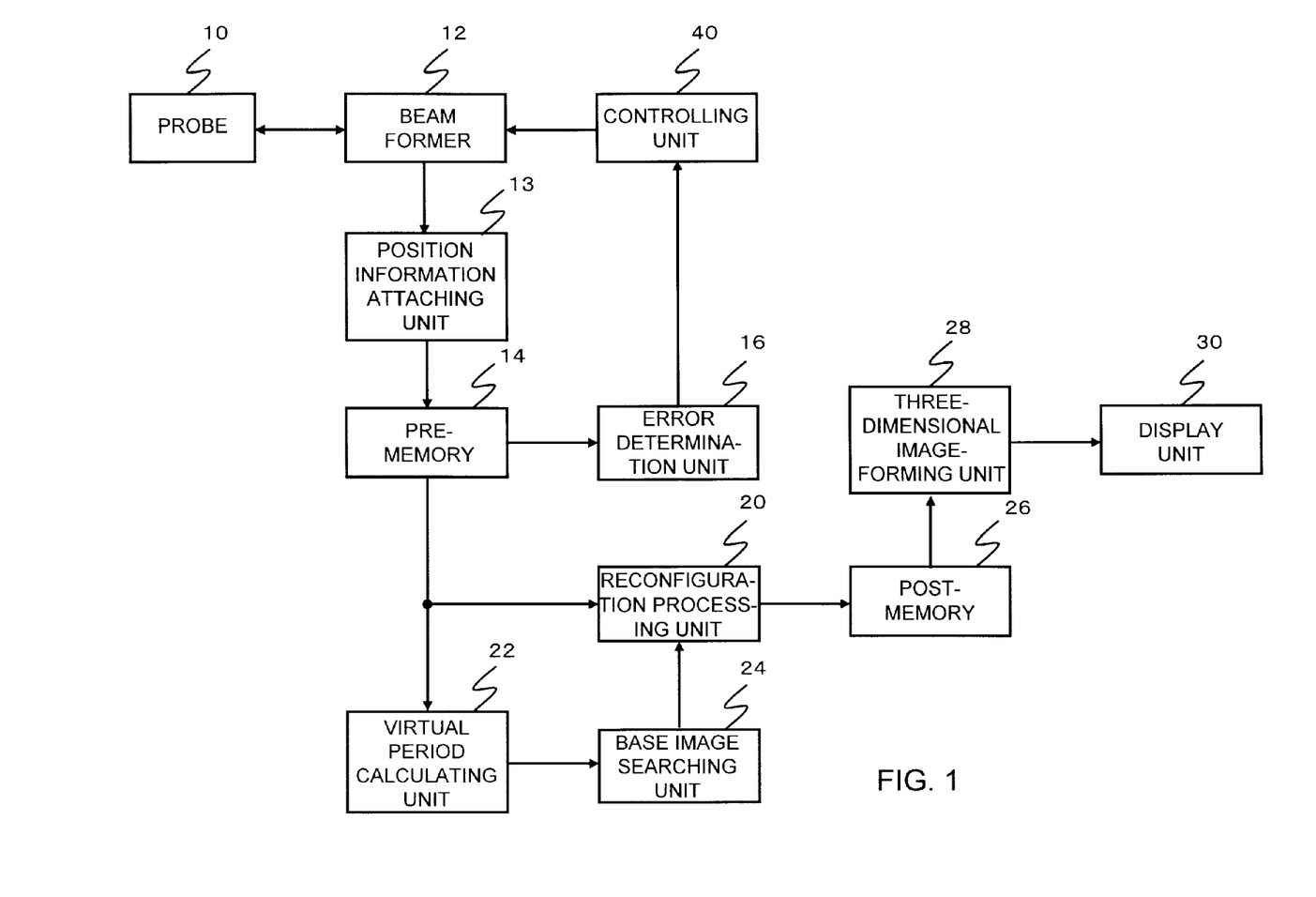
FIG. 1 is a diagram showing the overall structure of an ultrasound diagnostic apparatus according to a preferred embodiment of the present invention.

FIG. 1 is a diagram illustrating the overall configuration of an ultrasound diagnostic apparatus according to a preferred embodiment of the present invention. A probe 10 emits and receives ultrasonic waves within a three-dimensional region including an object. The probe 10 has a plurality of transducer elements that emit and receive ultrasonic waves and are controlled by a beam former 12 so as to form emission beams. The transducer elements also receive ultrasonic waves reflected from the object, and output signals obtained therefrom to the beam former 12, whereby the beam former 12 forms reception beams.

The probe 10 of the present embodiment is a 3D probe which scans ultrasonic beams (emission beams and reception beams) within the three-dimensional region and acquires echo data in three dimensions. For example, by mechanically moving a scanning plane which is electronically formed by transducer elements arranged in one dimension (1D array transducers), ultrasonic beams are scanned in three dimensions. Alternatively, it is also acceptable to electronically control transducer elements arranged in two dimensions (2D array transducers) so as to scan ultrasonic beams in three dimensions.

The beam former 12 forms emission beams of ultrasonic waves by supplying transmission signals corresponding to the respective transducer elements of the probe 10. Further, the beam former 12 forms reception beams of ultrasonic waves by applying a phasing addition process to reception signals obtained from the respective transducer elements of the probe 10, and outputs echo data acquired based on the reception beam.

In the present embodiment, an object is tissue in periodic motion or a fluid which varies on a periodic basis, such as the heart of a fetus or blood flowing through blood vessels of a fetus. As such, in the below description, a case where an object is the heart of a fetus, which is a preferred example, will be described. In the present embodiment, a scanning plane is displaced over a plurality of periods of motion of the object, which is the heart of a fetus, so that a plurality of scanning planes are formed within a three-dimensional region.

Figure 2:
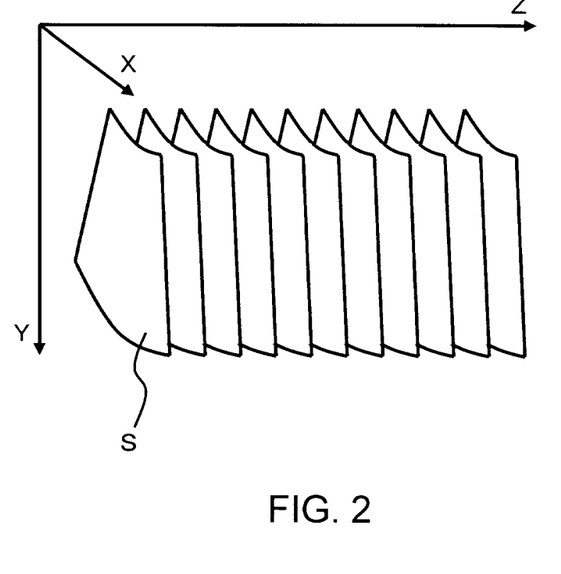
FIG. 2 is an illustration for explaining three-dimensional scanning in a preferred embodiment of the present invention.

FIG. 2 is an illustration explaining three-dimensional scanning in the present embodiment. In FIG. 2, a three-dimensional region containing an object is expressed in an X-Y-Z Cartesian coordinate system. In the present embodiment, for example, a scanning plane S is formed to be substantially parallel to the X-Y plane, and the scanning plane S is gradually displaced in the Z-axis direction such that a plurality of scanning planes S are formed along the Z-axis direction. The scanning plane S is gradually displaced in the Z-axis direction over a plurality of periods of the periodic motion of the object such as the heart of the fetus; that is, for example, over a time period in which almost 20 heartbeats are included in about eight seconds.

Turning back to FIG. 1, when a plurality of scanning planes are formed along the Z-axis direction over a plurality of periods of heartbeats of the fetus, data of tomographic images corresponding to the scanning planes are acquired, and a plurality of sets of the tomographic image data corresponding to the plurality of scanning planes are sequentially formed.

A position information attaching unit 13 attaches, to each set of tomographic image data acquired from each scanning plane, position information for identifying a position of the image data in the three-dimensional region. The position information attaching unit 13 obtains, for example, position information of the scanning planes which are sequentially formed along the Z-axis direction from the beam former 12 or a controlling unit 40, and attaches the position information of the scanning plane to the tomographic image data of each scanning plane. When the probe 10 is of a mechanically driven type in which the scanning plane is mechanically moved, the position information may alternatively be obtained from a position sensor or the like provided on the probe 10. Specific examples or the like of the position information will be described later in detail. The plurality of sets of tomographic image data to which the position information is attached are sequentially stored in a pre-memory 14.

An error determination unit 16 determines whether a plurality of sets of tomographic image data are favorable, based on the difference amount between images obtained from the plurality of sets of tomographic image data stored in the pre-memory 14. For example, there is a possibility that favorable images cannot be obtained because of large motion of the heart of the fetus within the images due to motion of the fetus, motion of the mother's body, or motion of the probe. As such, the error determination unit 16 determines whether or not images favorable for diagnosis are obtained. When determining, the error determination unit 16 utilizes a cross-sectional difference value which is defined by the following Equation 1:

$$\text{Cross-sectional difference value } [Z] = \sum_{x=0}^{m}\sum_{y=0}^{n} |p(x, y, z) - p(x, y, z+1)| \quad (1)$$

In Equation 1, x, y, and z represent coordinate values along the respective axes in the X-Y-Z Cartesian coordinate system, and p represents a pixel value corresponding to each coordinate within the tomographic image data. From Equation 1, a difference value between two adjacent sets of tomographic image data in the Z-axis direction is calculated.

Figure 3:
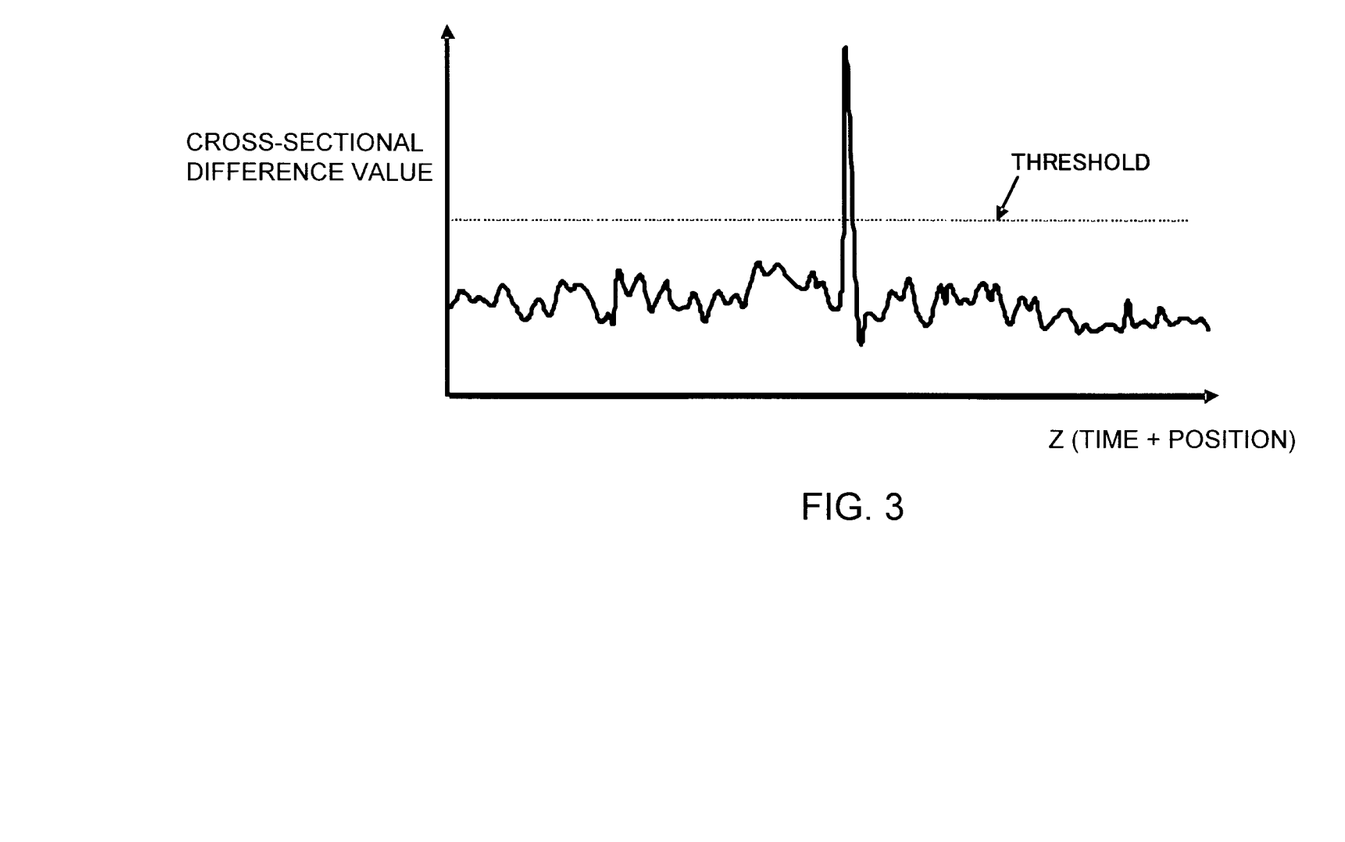
FIG. 3 is a graph showing changes in a cross-sectional difference value.

FIG. 3 is a graph showing changes in the cross-sectional difference value, in which the horizontal axis in FIG. 3 shows positions of respective sets of tomographic image data. In other words, the horizontal axis in FIG. 3 indicates the positions of the respective scanning planes and the times at which the respective scanning planes are obtained, which corresponds to the Z axis (displacement direction of the position with the elapse of time) in FIG. 2.

Without large motion of the heart of the fetus, adjacent sets of tomographic image data will be similar to each other, and a difference value obtained from Equation 1 will be relatively small. On the other hand, in the case where the fetus moves, the mother takes a breath, the position of the probe is displaced a long distance, or the like, the heart of the fetus moves a long distance within the tomographic images, so that a difference value between the adjacent sets of tomographic image data will be relatively large. As such, the error determination unit 16 determines that the heart moves a long distance in the image if a cross-sectional difference value exceeds a predetermined threshold.

Turning back to FIG. 1, when the error determination unit 16 determines that the object is displaced a long distance, the control unit 40 controls, for example, the beam former 12 to stop acquisition of the tomographic image data. It should be noted that the control unit 40 comprehensively controls each unit shown in FIG. 1, and when the error determination unit 16 determines that there is an error, for example, the control unit 40 may allow a display unit 30 to display the error or alert the operator of the error. When the error determination unit 16 does not determine that there is an error, the processes described below will be carried out based on a plurality of sets of tomographic image data stored in the pre-memory 14.

A virtual period calculating unit 22 calculates a virtual period, which serves as a temporary period relating to the heart of the fetus, based on the plurality of sets of the tomographic image data stored in the pre-memory 14. When calculating the virtual period, the virtual period calculating unit 22 uses a mutual difference value defined by the following Equation 2.

$$\text{Mutual Difference Value } [z] = \sum_{w=0}^{l}\sum_{x=0}^{m}\sum_{y=0}^{n} |p(x, y, z+w) \times \{p(x, y, z+w) - p(x, y, z+w+1)\}| \quad (2)$$

In Equation 2, x, y, and z represent coordinate values along the respective axes in the X-Y-Z Cartesian coordinate system, and p represents a pixel value corresponding to each coordinate within the tomographic image data. In Equation 2, a difference between two pixel values of two adjacent sets of tomographic image data in the Z-axis direction is multiplied by one of the pixel values. Thereby, the mutual difference value becomes larger when the heart dilates, as compared with the case where the heart contracts. As such, dilation and contraction, which are less likely to be distinguished by a simple difference value, can be distinguished by the mutual difference value.

For example, in tomographic image data set z, it is assumed that a pixel p(x, y, z) represents a cardiac muscle near the inner wall of the heart, and that the pixel value of p(x, y, z)=100. When the heart dilates and the cardiac cavity becomes larger, in tomographic image data set z+1 which is obtained following the tomographic image data set z, a pixel p(x, y, z+1) represents the cardiac cavity. As the pixel value of the cardiac cavity is smaller than that of the cardiac muscle, it is assumed that the pixel value of p(x, y, z+1)=10. In this example, the absolute value of the right side of Equation 2 is 100*(100−10)=9000. When the heart dilates, as pixels representing the cardiac muscle are changed to those representing the cardiac cavity in large proportion near the inner wall of the heart, the mutual difference value calculated from Equation 2 becomes relatively large.

On the contrary, when the heart contracts, a phenomenon opposite that of the above example will be caused. This means that as the cardiac cavity becomes smaller when the heart contracts, a pixel p(x, y, z)=10 corresponding to the cardiac cavity is changed to a pixel p(x, y, z+1)=100 corresponding to the cardiac muscle. In this example, the absolute value of the right side of Equation 2 is |10*(10−100)|=900, which is smaller than the value 9000 of the case of dilation. As such, dilation and contraction can be distinguished by the mutual difference value.

Figure 4:
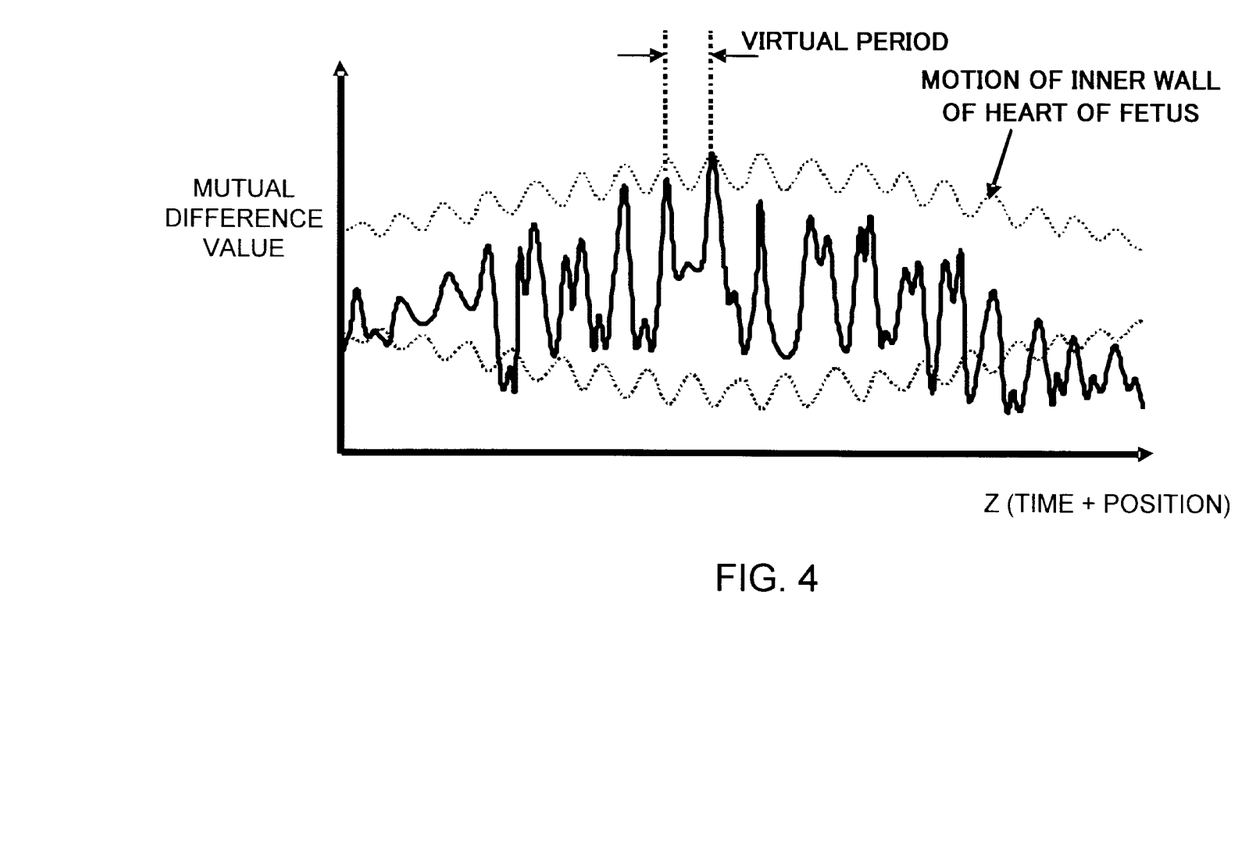
FIG. 4 is a graph showing changes in a mutual difference value.

FIG. 4 is a graph showing changes in the mutual difference value. In FIG. 4, the horizontal axis indicates positions of the respective sets of tomographic image data (positions and times of respective scanning planes), and corresponds to the Z axis (displacement direction of the position with the elapse of time) in FIG. 2. When mutual difference values are calculated at respective positions (z) on the Z axis from Equation 2, the mutual difference values become relatively large when the heart dilates. As such, the virtual period calculating unit 22 detects peak values (local maximum values) of the mutual difference values, and determines an interval between adjacent peak values to be a period of the heart (period of a heartbeat).

However, there is a case where the heartbeat period may vary, for example, in the heart of a fetus. When the heartbeat period varies, intervals between peak values also vary. As such, the virtual period calculating unit 22 sets a second largest interval among the intervals of peak values as a virtual period, for example. It should be noted that a value which occurs most frequently or a center-of-gravity value, which can be obtained from a histogram of intervals between peak values, may be set as a virtual period. Further, a user or the apparatus may select a virtual period among a plurality of preset values, or a user may input a value of a virtual period. Alternatively, a value obtained based on a measurement result of the ultrasound diagnostic apparatus (such as a result of an M mode measurement) may be used as the virtual period, or a fixed value may always be used as the virtual period.

Turning back to FIG. 1, when the virtual period is set, a base image searching unit 24 searches for a plurality of base images from the plurality of sets of tomographic image data using the virtual period.

Figure 5:
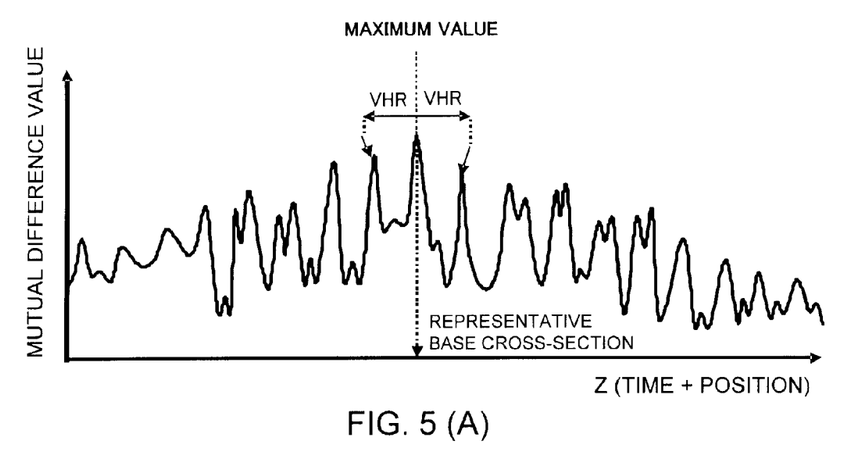
FIG. 5 shows graphs for explaining searches for base images.

FIG. 5 shows graphs for explaining searching of base images. FIGS. 5(A) to 5(C) respectively show changes in the mutual difference values which have been described by reference to FIG. 4. The base image searching unit 24 first searches for a base image serving as a representative (representative base image) from a plurality of tomographic images. As shown in FIG. 5(A), the base image searching unit 24 sets tomographic image data corresponding to the position where the mutual difference value becomes a maximum, as a representative base image (representative base cross-section). Then, the base image searching unit 24 uses the representative base image as a starting point to sequentially search for tomographic images, which are closest to the positions distant by the virtual period, from a plurality of tomographic images corresponding to the local maximum mutual difference values.

First, as shown in FIG. 5(A), the base image searching unit 24 searches for tomographic images which are closest to the positions distant from the representative base image by the virtual period (VHR) in the positive direction and the negative direction in the Z axis direction, and sets them as base images. Then, as shown in FIG. 5(B), the base image searching unit 24 searches for tomographic images which are closest to the positions distant from the searched base images by the virtual period (VHR) and sets them as new base images. In FIG. 5(B), arrows of broken lines show positions of a plurality of base images (base cross-sections).

The base image searching unit 24 uses the representative base image as a starting point and sequentially searches for a plurality of base images. In this way, a plurality of base images are searched from a plurality of tomographic images corresponding to the local maximum mutual difference values, as shown in FIG. 5(C). In FIG. 5(C), arrows of broken lines show the positions of a plurality of base images (base cross-sections).

Turning back to FIG. 1, when the plurality of base images have been searched, a reconfiguration processing unit 20 divides the plurality of tomographic images into a plurality of image groups, with the respective base images serving as the units for the division. Then, the reconfiguration processing unit 20 extracts, from the respective image groups, a plurality of tomographic images which correspond to one another on a periodic basis, to thereby realize the reconfiguration process (reconstruction process). The reconfiguration processing unit 20 reconfigures the plurality of sets of tomographic image data stored in the pre-memory 14 and stores them in a post-memory 26.

Figure 6:
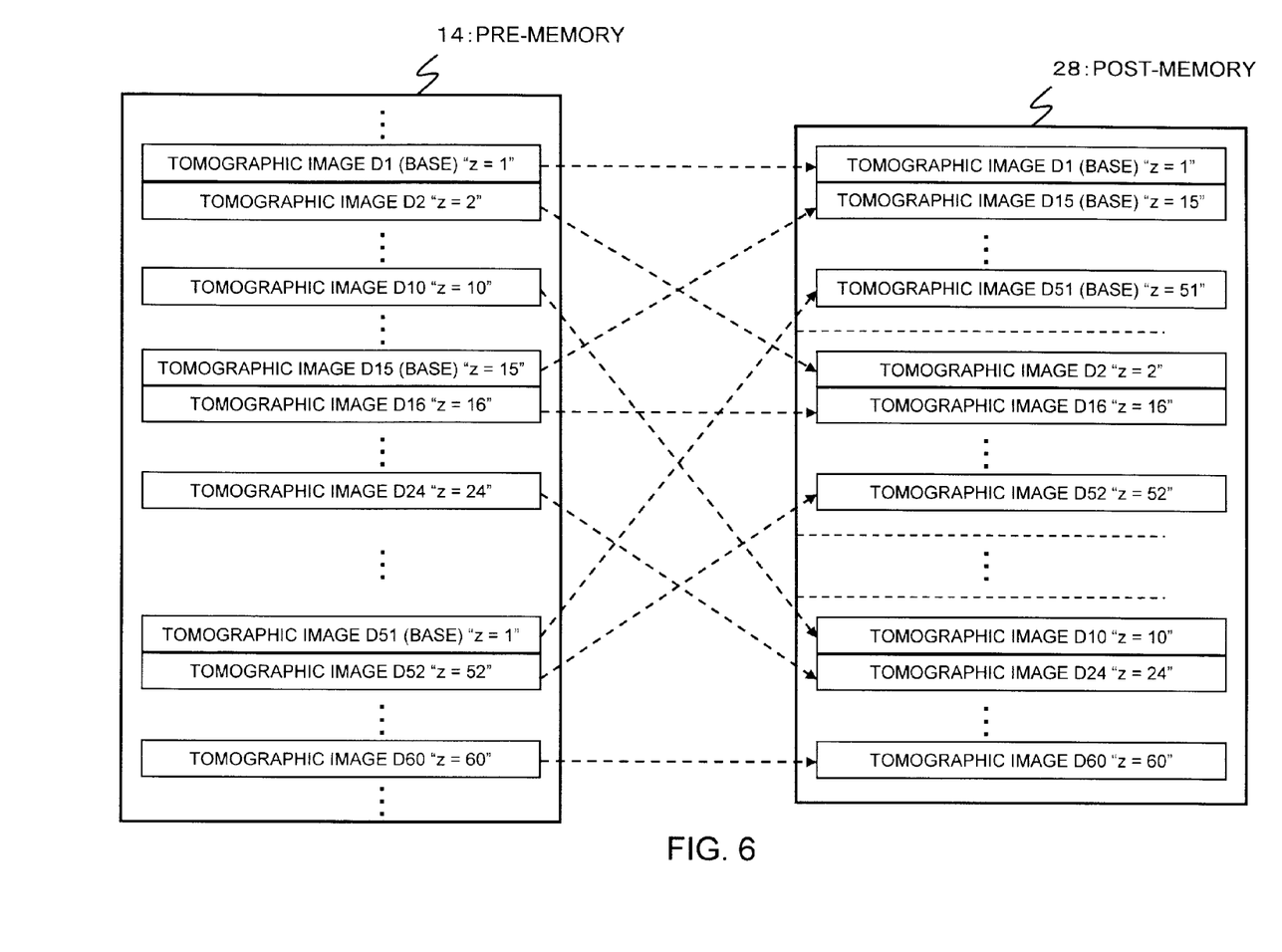
FIG. 6 is a diagram for explaining a set of processes performed by a reconfiguration processing unit.

FIG. 6 is a diagram for explaining a process performed by the reconfiguration processing unit 20. FIG. 6 shows a correspondence relationship between data to be stored in the pre-memory 14 and data to be stored in the post-memory 26. In FIG. 6, "tomographic images Dn (n=1, 2, 3, . . . , 60)" represent the plurality of sets of tomographic image data corresponding to the plurality of scanning planes formed along the Z axis (see FIG. 2).

In the pre-memory 14, a plurality of sets of tomographic image data corresponding to a plurality of scanning planes sequentially formed along the Z-axis direction are stored in the order of formation. This means that in the pre-memory 14, following some tomographic images, data of a plurality of tomographic images are stored in the order of a tomographic image D1, a tomographic image D2, . . . a tomographic image D60, . . . .

To the tomographic image data, position data z= 1, 2, 3, . . . , 60 are attached as position information of the tomographic image data in the three-dimensional region. The position data represent coordinate values on the Z-axis (see FIG. 2). For example, the tomographic image D1 corresponds to tomographic image data acquired from the scanning plane at a position of coordinate value 1 on the Z axis.

The reconfiguration processing unit 20 sets the respective base images as the division units to divide the plurality of sets of tomographic image data stored in the pre-memory 14 into a plurality of image groups. Then, a plurality of sets of tomographic image data which correspond to one another on a periodic basis are extracted from the image groups.

In FIG. 6, the tomographic image D1, a tomographic image D15, . . . , and a tomographic image D51 are a plurality of base images searched by the base image searching unit 24. The reconfiguration processing unit 20 first extracts the tomographic image D1, the tomographic image D15, . . . , and the tomographic image D51, which are bases images, as a plurality of sets of tomographic image data corresponding to one another on a periodic basis. Then, the extracted tomographic image D1, tomographic image D15, . . . , and tomographic image D51 are stored in the post-memory 26 as one data block.

Next, the reconfiguration processing unit 20 extracts a plurality of tomographic images, which are adjacent to the respective base images in the positive direction of the Z axis, as a plurality of sets of tomographic image data which correspond to one another on a periodic basis. As such, a tomographic image D2, a tomographic image D16, . . . , and a tomographic image D52 are extracted and stored in the post-memory 26 as one data block.

Further, the reconfiguration processing unit 20 extracts a plurality of tomographic images which are adjacent to the tomographic image D2, the tomographic image D16, . . . , and the tomographic image D52, respectively, in the positive direction of Z axis. In this way, with use of the respective base images as starting points, data blocks of a plurality of tomographic images corresponding to one another on a periodic basis are sequentially extracted and stored in the post-memory 26.

It should be noted that according to the above-described reconfiguration process, some tomographic images among the plurality of tomographic images stored in the pre-memory 14 are not used for the reconfiguration process. For example, tomographic images (D11 to D14) between the tomographic image D10 and the tomographic image D15 in the pre-memory 14 are not used for the reconfiguration process.

Further, in the above-described reconfiguration process, a plurality of data blocks are formed in the post-memory 26 after the reconfiguration process. For example, the tomographic image D1, the tomographic image D15, . . . , and the tomographic image D51 constitute one data block, and the tomographic image D2, the tomographic image D16, . . . , and the tomographic image D52 constitute the next data block. The number of data blocks formed in the post-memory 26 through the reconfiguration process corresponds to the number of tomographic images in an image group containing the smallest number of tomographic images, among a plurality of image groups formed by division according to the base images. For example, if a plurality of base images are searched as shown in FIG. 5(C), the number of tomographic images in an image group corresponding to a section having a shortest interval between two adjacent base images and the number of data blocks in the post-memory 26 shown in FIG. 6 conform with each other.

As such, after a plurality of base images are searched as shown in FIG. 5(C), by checking the number "e" of the tomographic images in an image group corresponding to a section having the shortest interval between two adjacent base images, setting the number as the number "e" of the data blocks, and ending the reconfiguration process when the number of the data blocks reaches "e" as a result of the reconfiguration process, for example, it is possible to reduce (desirably, to completely eliminate) unnecessary steps in the reconfiguration process.

In addition, although in the example configuration shown in FIG. 6 a data block corresponding to the base images is set as the first data block of the plurality of data blocks, the plurality of data blocks may alternatively be formed such that the data block corresponding to the base images is at a desired position. For example, the data block corresponding to the base images may be set as the center.

Turning back to FIG. 1, a three-dimensional image-forming unit 28 forms three-dimensional image data showing the object such as the heart of the fetus in three dimensions, based on the plurality of sets of tomographic image data after the reconfiguration and storage in the post-memory 26. The three-dimensional image-forming unit 28 forms the three-dimensional image data of each time phase based on one data block stored in the post-memory 26. For example, three-dimensional image data of a time phase T1 is formed based on the tomographic image D1, the tomographic image D15, . . . , and the tomographic image D51 stored in the post-memory 26 shown in FIG. 6, and three-dimensional image data of a time phase T2 is formed based on the tomographic image D2, the tomographic image D16, . . . , and the tomographic image D52 stored in the post-memory 26.

The three-dimensional image-forming unit 28 forms the three-dimensional image data over a plurality of time phases and for each time phase by means of any of various methods such as, for example, a volume rendering method, an integration method, and a projection method. An image corresponding to the three-dimensional image data formed over the plurality of time phases in this manner is displayed on the display unit 30, and a three-dimensional moving image is displayed in a pseudo manner in a real time basis. For example, images corresponding to three-dimensional image data from the time phase T1 to a final time phase Te may be displayed repeatedly to thereby perform loop reproduction.

In the present embodiment, when the three-dimensional image data are formed from the plurality of sets of tomographic image data which correspond to one another on a periodic basis, each set of the tomographic image data is correlated to a position identified by respective position data.

Figure 7:
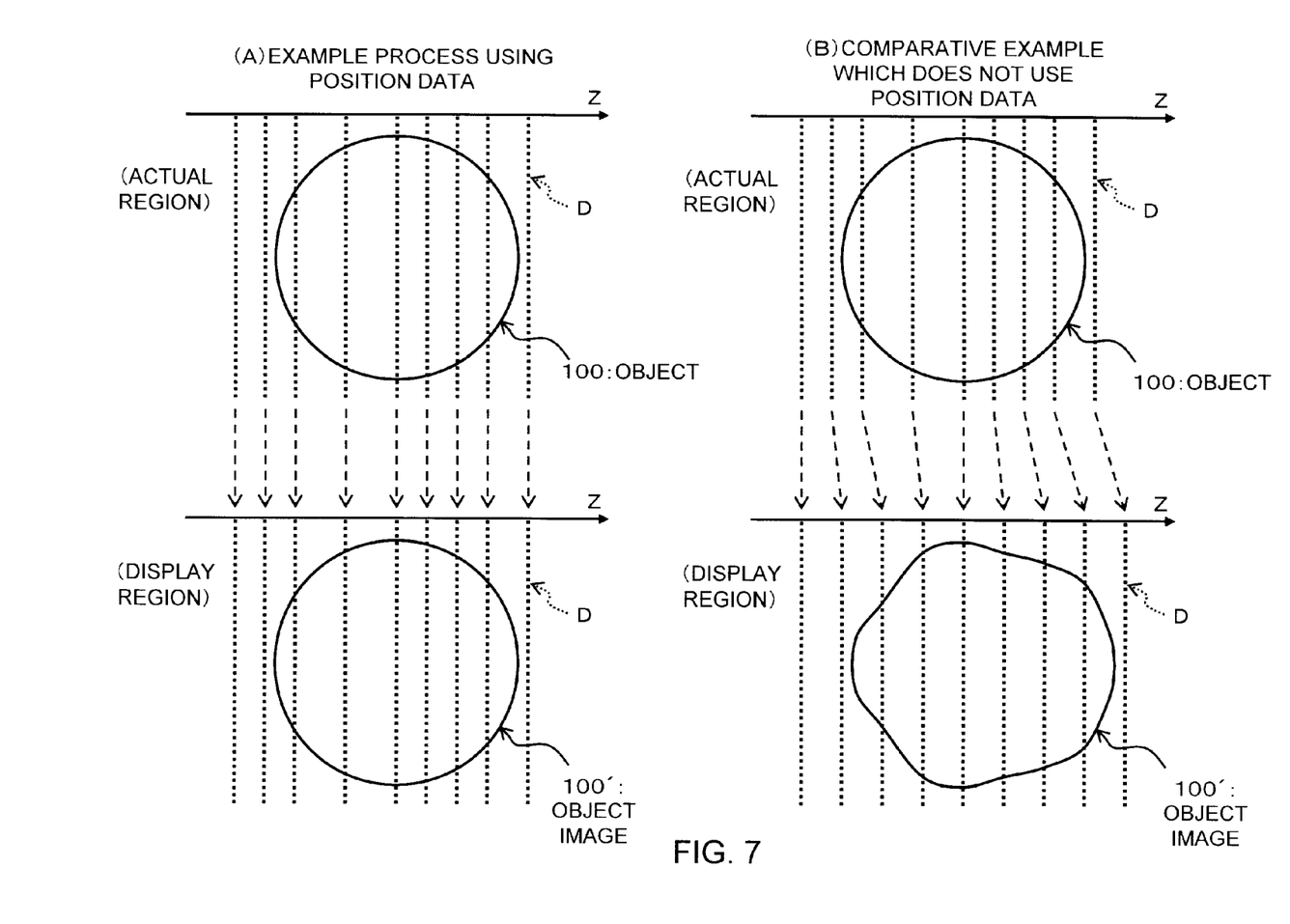
FIG. 7 is a diagram showing an example process of image formation using position data.

FIG. 7 is a diagram showing an example process of image formation using position data. An actual region shown in FIG. 7 is a region where an object 100 such as the heart actually exists, and is, for example, the three-dimensional region shown in FIG. 2. The display region shown in FIG. 7 is a three-dimensional data region in which three-dimensional image data containing an object image 100' is formed.

FIG. 7(A) shows an example process using the position data in the present embodiment. A plurality of tomographic images D shown with broken straight lines in the actual region represent a plurality of sets of tomographic image data which correspond to one another on a periodic basis. For example, the tomographic image D1, the tomographic image D15, . . . , the tomographic image D51 collected as one data block in the post-memory 26 shown in FIG. 6 correspond to the plurality of tomographic images D in FIG. 7(A).

In the present embodiment, because an appropriate base image is searched for according to the variation in the period of motion of the object 100 such as the heart, the spatial distance of the plurality of tomographic images D may vary, as shown in the actual region of FIG. 7(A). In consideration of this, in the present embodiment, the three-dimensional image data to become the display image are formed while correlating each of the plurality of tomographic images D obtained from the actual region to the position in the display region identified by the position data. For example, because the position data of the tomographic image D1 are z=1 (see FIG. 6), the tomographic image D1 is placed at the position of z=1 also in the display region. Similarly, the other tomographic images D are placed at positions according to the position data of the respective tomographic images D.

With this configuration, as shown in FIG. 7(A), the plurality of tomographic images D are placed in the display region while maintaining the position of each of the plurality of tomographic images D in the actual region and maintaining the distance between the tomographic images D in the actual region. Based on the plurality of tomographic images D placed in the display region, three-dimensional image data containing the object image 100' are formed. Because the arrangement state of the plurality of tomographic images D in the actual region is maintained also in the display region, the object image 100' is formed while maintaining the true shape of the object 100.

On the other hand, FIG. 7(B) shows a comparative example which does not use the position data. In FIG. 7B) also, the plurality of tomographic images D shown with broken straight lines in the actual region represent the plurality of sets of tomographic image data which correspond to one another on a periodic basis. The shape of the object 100 shown in the actual region and the arrangement state of the plurality of tomographic images in the actual region are identical between FIGS. 7(A) and 7(B).

In the comparative example of FIG. 7(B), the plurality of tomographic images D obtained from the actual region are arranged in equal spacing in the display region, to thereby form the three-dimensional image data to become the display image. If the plurality of tomographic images D are placed at equal distances in the display region despite variation in the spatial distance among the plurality of tomographic images D in the actual region, the true shape of the object 100 cannot be maintained, and an object image 100' which is distorted from the true shape is formed.

As can be understood from a comparison of FIGS. 7(A) and 7(B), in the present embodiment, with the use of the position data, the object image 100' can be formed while maintaining the true shape of the object 100.

There are some cases where the scanning coordinate system of the ultrasonic beam and the display coordinate system of the display image are not in simple similarity relationship. For example, in the case of a scanning of a convex type, a scanning plane formed in a fan shape is scanned along a scanning direction of an arc shape, to form a plurality of tomographic images. The plurality of tomographic images formed in this manner may be placed in a display region of, for example, the X-Y-X Cartesian coordinate system, to form the three-dimensional image data. In this case, pixel values of coordinates in the display region are formed through an interpolation process or the like based on the plurality of echo data constituting the plurality of tomographic images.

Figure 8:
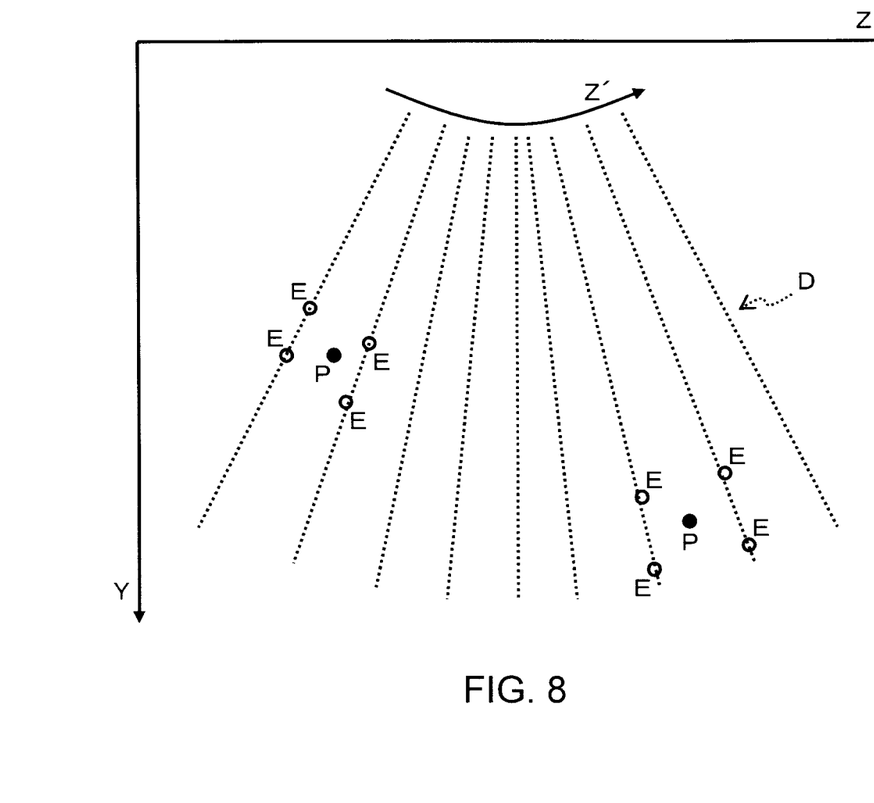
FIG. 8 is a diagram for explaining a formation process of three-dimensional image data involving an interpolation process.

FIG. 8 is a diagram for explaining a formation process of three-dimensional image data involving an interpolation process. A Z axis and a Y axis in FIG. 8 are axes of a display coordinate system expressed in the X-Y-Z Cartesian coordinate system. A Z' axis in an arc shape corresponds to the scan direction of the scanning plane, and a plurality of tomographic images D are formed along the Z' axis. The tomographic images D shown in FIG. 8 are a plurality of tomographic images which correspond to one another on a periodic basis, and the spatial distance may not be constant. Therefore, in the scanning form shown in FIG. 8 also, each of the plurality of tomographic images D is placed in the display coordinate system in correlation to the position identified by respective position data.

In the scanning form shown in FIG. 8, pixel values of coordinates in the display coordinate system are formed based on the echo data in the tomographic image and with an interpolation process. Specifically, a pixel value P at a certain coordinate in the display coordinate system is formed by the interpolation process based on a plurality of echo data E for positions near the pixel value P. For example, the pixel value P is determined based on 8 sets of echo data E which are spatially adjacent to the pixel value P. In FIG. 8, of the 8 sets of echo data adjacent to the pixel value P, only 4 sets of echo data are shown.

The pixel value P is determined in this manner for all coordinates in the display coordinate system, and the three-dimensional image data are formed based on these pixel values P. In the scanning form shown in FIG. 8 also, because each of the plurality of tomographic images D is placed in the display coordinate system in correlation to the position identified by the respective position data, the object image can be formed while maintaining the true shape of the object.

The formation of the pixel values by the interpolation process explained with reference to FIG. 8; that is, the process to map the echo data in the tomographic image to the display region, is performed, for example, by the three-dimensional image-forming unit 28. For example, as a result of the reconfiguration process by the reconfiguration processing unit 20, the plurality of tomographic image (data) after the reconfiguration shown in FIG. 6 are stored in the post-memory 26, and the three-dimensional image-forming unit 28 performs the mapping process shown in FIG. 8 based on the plurality of tomographic images after the reconfiguration process shown in FIG. 6.

Alternatively, the reconfiguration processing unit 20 may perform the mapping process. Specifically, after the reconfiguration processing unit 20 performs the reconfiguration process, the reconfiguration processing unit 20 may perform the mapping process shown in FIG. 8 using the plurality of tomographic images after the reconfiguration process, and store the data mapped to the display coordinate system in the post-memory 26.

A preferred embodiment of the present invention has been described. According to the above-described embodiment, even when an object having a periodic motion with an unstable period such as, for example, the heart of the fetus, is to be diagnosed, because the appropriate base images are searched for according to the variation in the period and the data block is reconfigured, temporal disturbances of the display image due to the variation in the period are reduced, or, desirably, completely eliminated. In addition, because the display image is formed while the plurality of tomographic images are placed at appropriate positions using the position data, spatial distortion of the display image or the like is also reduced, or, desirably, completely eliminated.

As described, according to the present embodiment, a very highly reliable display image can be obtained by reducing or eliminating the temporal disturbance and reducing or eliminating the spatial distortion.

The above-described embodiment is merely exemplary in every aspect, and does not limit the scope of the present invention. For example, in the above-described embodiment, low-speed scanning is performed in which the scanning plane is gradually displaced along the Z-axis direction to form a plurality of scanning planes, and echo data are acquired from the three-dimensional region, but alternatively, it is also possible to employ a configuration where, before the low-speed scanning, the three-dimensional region is experimentally scanned with high speed such as with a round trip of about 2 seconds, to assist in designation of the probe position.

What is claimed is:

1. An ultrasound diagnostic apparatus comprising:
    a probe that emits and receives ultrasonic waves to and from a three-dimensional region including an object in periodic motion;
    an emission and reception controlling unit that controls the probe such that a scanning plane is displaced over a plurality of periods of the motion so as to form a plurality of scanning planes within the three-dimensional region;
    a base image searching unit that searches for a plurality of base images from an image string constituted of a plurality of images corresponding to the plurality of scanning planes based on a feature amount relating to the periodicity of the motion;
    an image reconfiguration unit that divides the image string into a plurality of image groups using the respective base images as dividing units, and extracts from the respective image groups a plurality of images which correspond to one another on a periodic basis; and
    a display-image-forming unit that forms a display image of the object based on the plurality of images which correspond to one another on a periodic basis, wherein
    position information for identifying a position of an image in the three-dimensional region is attached to each image obtained from each of the scanning planes, and
    the display image is formed while each of the plurality of images which correspond to one another on a periodic basis is correlated to a position within a display region identified by respective position information.

2. The ultrasound diagnostic apparatus according to claim 1, further comprising a position information attaching unit that attaches the position information to each image obtained from each of the scanning planes.

3. The ultrasound diagnostic apparatus according to claim 1, wherein
    the image reconfiguration unit extracts the plurality of images which correspond to one another on a periodic basis from the respective image groups to change the order of the images in the image string to form a reconfigured image string, and
    the display-image-forming unit forms the display image based on the plurality of images which correspond to one another on a periodic basis obtained from the reconfigured image string and while correlating each of the plurality of images which correspond to one another on a periodic basis to a position within the display region identified by the respective position information.

4. The ultrasound diagnostic apparatus according to claim 3, further comprising a position information attaching unit that attaches the position information to each image obtained from each of the scanning planes.

5. The ultrasound diagnostic apparatus according to claim 1, wherein
    the image reconfiguration unit extracts the plurality of images which correspond to one another on a periodic basis from the respective image groups to change the order of the images in the image string to form a reconfigured image string while correlating each of the extracted images to a position within the display region identified by the respective position information, and
    the display-image-forming unit forms the display image based on the plurality of images which correspond to one another on a periodic basis obtained from the reconfigured image string.

6. The ultrasound diagnostic apparatus according to claim 5, further comprising a position information attaching unit that attaches the position information to each image obtained from each of the scanning planes.

7. The ultrasound diagnostic apparatus according to claim 1, wherein
    the base image searching unit searches for the plurality of base images from the plurality of images constituting the image string at an interval corresponding to a virtual period of the motion of the object.

8. The ultrasound diagnostic apparatus according to claim 7, wherein
    the base image searching unit sets a representative base image from the plurality of images based on the feature amount, and searches for the plurality of base images using the representative base image as a starting point.

9. The ultrasound diagnostic apparatus according to claim 8, wherein
    the base image searching unit sets an image corresponding to a maximum mutual difference value, among mutual difference values of the respective images constituting the image string, as the representative base image, and with use of the representative base image as the starting point, sequentially searches for images which are closest to a position distant by the virtual period from a plurality of images corresponding to local maximum mutual difference values, and sets the images as the plurality of base images.

10. The ultrasound diagnostic apparatus according to claim 1, wherein
    the base image searching unit searches for the plurality of base images from the plurality of images constituting the image string at an interval corresponding to a virtual period of the motion of the object,
    the image reconfiguration unit extracts the plurality of images which correspond to one another on a periodic basis from the respective image groups to change the order of the images in the image string to form a reconfigured image string, and
    the display image forming unit forms the display image based on the plurality of images which correspond to one another on a periodic basis obtained from the reconfigured image string and while correlating each of the plurality of images which correspond to one another on a periodic basis to a position within the display region identified by the respective position information.

11. The ultrasound diagnostic apparatus according to claim 10, wherein
    the base image searching unit sets a representative base image from the plurality of images based on the feature amount, and searches for the plurality of base images using the representative base image as a starting point.

12. The ultrasound diagnostic apparatus according to claim 11, wherein
    the base image searching unit sets an image corresponding to a maximum mutual difference value, among mutual difference values of the respective images constituting the image string, as the representative base image, and with use of the representative base image as the starting point, sequentially searches for images which are closest to a position distant by the virtual period from a plurality of images corresponding to local maximum mutual difference values, and sets the images as the plurality of base images.

13. The ultrasound diagnostic apparatus according to claim 1, wherein the base image searching unit searches for the plurality of base images from the plurality of images constituting the image string at an interval corresponding to a virtual period of the motion of the object, the image reconfiguration unit extracts the plurality of images which correspond to one another on a periodic basis from the respective image groups to change the order of the images in the image string to form a reconfigured image string while correlating each of the extracted images to a position within the display region identified by the respective position information, and the display-image-forming unit forms the display image based on the plurality of images which correspond to one another on a periodic basis obtained from the reconfigured image string.

14. The ultrasound diagnostic apparatus according to claim 13, wherein the base image searching unit sets a representative base image from the plurality of images based on the feature amount, and searches for the plurality of base images using the representative base image as a starting point.

15. The ultrasound diagnostic apparatus according to claim 14, wherein the base image searching unit sets an image corresponding to a maximum mutual difference value, among mutual difference values of the respective images constituting the image string, as the representative base image, and with use of the representative base image as the starting point, sequentially searches for images which are closest to a position distant by the virtual period from a plurality of images corresponding to local maximum mutual difference values, and sets the images as the plurality of base images.

* * * * *